(12) United States Patent
Palm et al.

(10) Patent No.: US 8,927,276 B2
(45) Date of Patent: Jan. 6, 2015

(54) EX VIVO PROGENITOR AND STEM CELL EXPANSION AND DIFFERENTIATION FOR USE IN THE TREATMENT OF DISEASE OF THE NERVOUS SYSTEM

(75) Inventors: Kaia Palm, Tallinn (EE); Toomas Neuman, Tallinn (EE)

(73) Assignee: Cellin Technologies OUE, Tallinn (EE)

(*) Notice: Subject to any disclaimer, the term of this patent is extended or adjusted under 35 U.S.C. 154(b) by 566 days.

(21) Appl. No.: 12/707,607

(22) Filed: Feb. 17, 2010

(65) Prior Publication Data
US 2011/0201113 A1    Aug. 18, 2011

(51) Int. Cl.
    *C12N 5/07*      (2010.01)
    *C12N 5/10*      (2006.01)
    *C12N 5/00*      (2006.01)
    *A61K 35/30*     (2006.01)
    *C12N 5/0797*    (2010.01)

(52) U.S. Cl.
CPC ........ *C12N 5/0623* (2013.01); *C12N 2501/115* (2013.01); *C12N 2506/08* (2013.01); *C12N 2501/235* (2013.01); *C12N 2501/148* (2013.01); *C12N 2501/11* (2013.01)
USPC ........... 435/368; 435/363; 435/366; 435/384; 435/392; 435/402; 435/405; 424/93.7; 424/570

(58) Field of Classification Search
CPC ................. C12N 2506/08; C12N 2501/148; C12N 2501/11
USPC ......... 435/368, 363, 366, 384, 392, 402, 405; 424/93.7, 570
See application file for complete search history.

(56) References Cited

U.S. PATENT DOCUMENTS 5,411,883 A * 5/1995 Boss et al. ...................... 435/29
5,968,829 A * 10/1999 Carpenter ..................... 435/467

OTHER PUBLICATIONS

Reubinoff BE et al., Nat Biotechnol. Dec. 2001;19(12):1134-40. Neural progenitors from human embryonic stem cells.*

* cited by examiner

*Primary Examiner* — Maria Leavitt
(74) *Attorney, Agent, or Firm* — Wagenknecht IP Law Group PC

(57) ABSTRACT

The present invention relates to a simplified process, which is shorter in time, for propagation of proliferating cells, such as e.g. progenitor or stem cells, by means of a biphasic culturing system having a differentiation supporting component and a proliferation supporting component, and to the use of the stem cell cultures obtained in this way for cell therapy purposes. The present invention invention describes a method, which is highly efficient to prime stem or progenitor cells to differentiation using non-attachment matrices and differentiation supporting component. The cells produced therefrom may be used to treat a variety of neurodegenerative disorders.

10 Claims, 13 Drawing Sheets

The biphasic culture system of human NSCs.

The biphasic culture system of human NSCs varying the growth factors.

SEQUENCE LISTING

```
<160> NUMBER OF SEQ ID NOS: 58

<210> SEQ ID NO 1
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 1
ggccttcctg caagtcacc                                               19

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 2
atcgtctcgg ggaacacagt                                              20

<210> SEQ ID NO 3
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 3
acgttttgaa gggaccagta cg                                           22

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 4
cactcacaat ctcccattct cc                                           22

<210> SEQ ID NO 5
<211> LENGTH: 23
<212> TYPE: DNA
<213> ORGANISM: ARTIFICIAL SEQUENCE
<220> FEATURE:
```

<223> OTHER INFORMATION: SYNTHETIC CONSTRUCT

<400> SEQUENCE: 5
tgacatcgtg ctttacaaca acg                                    23

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 6
cgtgtggtca taggtccagg                                        20

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 7
agtggctgtt gccaattatg c                                      21

<210> SEQ ID NO 8
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 8
ggactgaccc ctaatacagg tt                                     22

<210> SEQ ID NO 9
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 9
gtcactgtta catgaccagc c                                      21

<210> SEQ ID NO 10
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 10
cgtccagaag acgatccaag at                                     22

<210> SEQ ID NO 11
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 11
agaaaaacaa cacttacgct cca                                    23

```
<210> SEQ ID NO 12
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12
gggcttgacc tctttaggtt c                                              21

<210> SEQ ID NO 13
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 13
gtacaaaatc gagagagtct ggg                                            23

<210> SEQ ID NO 14
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14
gcgaatgtca tatcctttga gca                                            23

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 15
cttgacaatc gagtggctga                                                20

<210> SEQ ID NO 16
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 16
caatcctttc cactccggta                                                20

<210> SEQ ID NO 17
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 17
acatcgtgat cgtgtagtcc a                                              21

<210> SEQ ID NO 18
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT
```

<400> SEQUENCE: 18
tcccgaaatt ccacttcgag t                                     21

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 19
tgcctgccag agtttcactg                                       20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 20
cacacatgca cgggaacttc                                       20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 21
gccctacctg agctactacc                                       20

<210> SEQ ID NO 22
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 22
gaggatcatg cgtgtcacct t                                     21

<210> SEQ ID NO 23
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 23
cagtgaacgt gagctgcaac                                       20

<210> SEQ ID NO 24
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 24
tccagagagt cgtcagggta t                                     21

<210> SEQ ID NO 25
<211> LENGTH: 23

```
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 25
tcgggatttt acttctggga agc                                    23

<210> SEQ ID NO 26
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 26
gatagagccg aaactgttga tga                                    23

<210> SEQ ID NO 27
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 27
ggtctgccct gagaaatcca g                                      21

<210> SEQ ID NO 28
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 28
ctcgcccttg tcgtaccac                                         19

<210> SEQ ID NO 29
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 29
aggaacccct cggacaagtt                                        20

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 30
ctctccagtc gtcaccaggt                                        20

<210> SEQ ID NO 31
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 31
```

```
tgggtcctag ccatcaccat t                                         21
```

<210> SEQ ID NO 32
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 32

```
gccctgaaga gtgaaattcc a                                         21
```

<210> SEQ ID NO 33
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 33

```
atgggtccaa taggtgcaga g                                         21
```

<210> SEQ ID NO 34
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 34

```
agcagtaggc caatatgaga aca                                       23
```

<210> SEQ ID NO 35
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 35

```
ggtcctgggt aacctctgc                                            19
```

<210> SEQ ID NO 36
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 36

```
gagaccgtca ccgacatgc                                            19
```

<210> SEQ ID NO 37
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 37

```
gctcaactac gaactcccta atg                                       23
```

<210> SEQ ID NO 38
<211> LENGTH: 20
<212> TYPE: DNA
<213> ORGANISM: ARTIFICIAL SEQUENCE

-continued

```
<220> FEATURE:
<223> OTHER INFORMATION: SYNTHETIC CONSTRUCT

<400> SEQUENCE: 38
agaggcaccc ttcacaggaa                                              20

<210> SEQ ID NO 39
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 39
gcttgccaga aaggtgaaa tc                                            22

<210> SEQ ID NO 40
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 40
ggcggatgac cacatagaac tt                                           22

<210> SEQ ID NO 41
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 41
gtcacccgaa tggtgtccat c                                            21

<210> SEQ ID NO 42
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 42
atttgtcctg cttactgtca ctc                                          23

<210> SEQ ID NO 43
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 43
cacaacgaat ggtactacgg c                                            21

<210> SEQ ID NO 44
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 44
ctctgctggg catggtctc                                               19
```

<210> SEQ ID NO 45
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 45
cgtaagatgg cagcaaaaac tc                                        22

<210> SEQ ID NO 46
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 46
gccaggcggt tgttgagat                                            19

<210> SEQ ID NO 47
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 47
gccaaacaga agggatatgt tcc                                       23

<210> SEQ ID NO 48
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 48
gcccatcatc ttgtgagggt t                                         21

<210> SEQ ID NO 49
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 49
ggcttttggt ctttcgggtc                                           20

<210> SEQ ID NO 50
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 50
ttctcggcgt ctccgtagag                                           20

<210> SEQ ID NO 51
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 51
gagacgtttg aagccaaaat cc                                              22

<210> SEQ ID NO 52
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 52
aggtcagggt cgaacttggt                                                 20

<210> SEQ ID NO 53
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 53
actggctact gcacggacaa g                                               21

<210> SEQ ID NO 54
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 54
ctttctccca gtcaggtgtg tgt                                             23

<210> SEQ ID NO 55
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 55
cagcagccga tgacacact                                                  19

<210> SEQ ID NO 56
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 56
gcacgaagtc tgtctggatg g                                               21

<210> SEQ ID NO 57
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 57
cagcagcaaa ggtcaccag                                                  19

<210> SEQ ID NO 58

```
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 58
ggctgttagt cagggactga g                                          21
```

EX VIVO PROGENITOR AND STEM CELL EXPANSION AND DIFFERENTIATION FOR USE IN THE TREATMENT OF DISEASE OF THE NERVOUS SYSTEM

FIELD OF THE INVENTION

The present invention relates to in vitro methods for expansion of nervous system-derived progenitor and stem cells (NSC's) into neuronal cells. Specifically, methods of ex-vivo expansion of nervous system-derived progenitor and stem cells, expanded populations of renewable progenitor and stem cells and their uses in therapeutic applications such as treatments of a variety of diseases, including neurotrauma and/or neurodegenerative diseases.

BACKGROUND OF THE INVENTION

The mammalian, including human, central nervous system (CNS, brain and spinal cord) has an extremely low ability for spontaneous anatomical and functional recovery after injury. This inability of the CNS to regenerate is due to a lack of a natural way to replace lost neurons and to establish intense functional connections between different neuronal populations after trauma. It has been demonstrated that central nervous system contains multipotent progenitor cells. These multipotent cells proliferate and differentiate into neurons, astrocytes and oligodendrocytes in vitro and in vivo. Progenitor cells or neuronal derivatives of these cells can be used for transplantation to stimulate anatomical and functional regeneration. Cell replacement and neuronal circuitry reconstruction strategies in human neurological conditions require a well-established source of neuronal cells. Techniques have been developed to isolate, propagate and differentiate neuronal stem cells from the fetal and adult human central nervous system. Unfortunately, propagation of these stem cells is time consuming (many months) and during propagation many cells loose their multipotency to differentiate in variety of neuronal types.

One of the crucial problems in cell therapy using autologous transplantable cells is propagation of neural stem cells in conditions that will result in a large number of multipotent cells whereas cells maintain the capacity to differentiate into variety of neural cell types. Numerous data clearly show that there is a balance between multipotent neural stem cell population and populations of neural progenitor cells (NPC) that are committed to certain differentiation pathway both in vivo and in vitro.

With regard to development, it is well established that different signaling routes (Wnt, Shh and BMP/TGFbeta, Notch and TK signaling cascades) are critical for proper gene expression at appropriate times since antagonistics biological processes, such as proliferation-differentiation and survival-apoptosis, are all integrated in the formation of a three-dimensional nervous (brain) tissue, whose function changes with time. In embryonic stages, the growth and proper development of nervous structures is dependent on the interaction between the glial cells and neurons and require the concerted actions of various bioactive peptides and hormone-like substances, and cell-cell and cell-substrate interactions. The necessity for these complex structural and hormonal interactions provide a challenge for the development of in vitro cell culture models that more accurately mimic the developing nervous system.

Similarly, the mammalian central nervous system (CNS; brain and spinal cord) has a limited ability for spontaneous recovery following an injury. This inability of the CNS to regenerate is caused by the lack of a natural pathway to replace lost neurons and re-establish the functional connections between different neuronal populations after trauma.

However, it has been demonstrated that the CNS contains multipotent progenitor cells (nervous system-derived progenitor and stem cells; NSC's) that can proliferate and differentiate into neurons, astrocytes and oligodendrocytes both in vitro and in vivo. Progenitor cells (or neuronal derivatives of these cells) can be transplanted to stimulate anatomical and functional regeneration. Techniques have been developed to isolate, propagate and differentiate neuronal stem cells from the CNS, but propagation of these stem cells is time consuming (typically many months) and many cells lose their multipotency to differentiate as a result of the process.

Current culture models using continuous exposure of cultured NSC's to high levels of bFGF (basic Fibroblast Growth Factor), LIF (Leukemia Inhibitory Factor) and EGF (Epidermal Growth Factor) have not yielded substantial numbers of human NSC's (hNSC's) in vitro, thus preventing the use of propagated hNSCs for autologous transplantation purposes. Therefore, there exists a need for methods of expansion of hNSC's into neuronal cells.

SUMMARY OF THE INVENTION

Embodiments of the present invention provide methods and systems for biphasic culturing of hNSCs and further differentiation. The differentiation can result in neuronal cells or glial cells, and can provide related benefits. In some embodiments a pluripotent stem cell is obtained. In some embodiments a multipotent stem cell is obtained. In some embodiments a cell having characteristics of a neuronal cell is obtained. In some embodiments a cell having characteristics of a neural crest stem cell is obtained. In other embodiments neuronal cells or glial cells are obtained. The cells obtained by methods of the present invention can be used in various medical treatments where repair or formation of neurons is desired. In some embodiments, cells according to the present invention are used to treat or reduce neuron degradation or the rate of neuron degradation. In some embodiments cells of the present invention are useful for the treatment or prevention of, for example, neurodegenerative disorders, neurotrauma, Alzheimer's disease, Parkinson's disease, and the like. In other embodiments compounds suspected of affecting differentiation or development of neural stem cells or neuronal cells are studied using the methods or cells of the present invention. Differentiated cells of the present invention can be obtained by providing a population of neural stem cells/neurospheres and exposing the neural stem cells/neurospheres to conditions that affect or direct differentiation potential. Such conditions can include, for example, altering the surrounding growth factor composition of the media or environment and providing or eliminating an appropriate supporting growth matrix or substrate.

Embodiments of the invention provide methods of optimized in vitro growth (propagation) of hNSC's, enabling rapid growth without loss of multipotency.

Embodiments of the invention provide techniques to propagate human neural stem cells ("hNSCs") as multipotent cells in significant numbers and then, for example, hNSCs differentiate the cells into particular types of nervous system cells. Certain embodiments include a method of fast propagation of hNSCs utilizing dynamic incubation of cells in a biphasic culture system where cells are initially grown for a set time interval, such as, for example, 1 day, 2 days, 3 days, 4 days, 6 days, 7 days, or more, or the like.

In certain embodiments, during the initial growth period the cells can be cultured with, for example, combinations of different bioactive molecules such as growth factors epidermal growth factor ("EGF"), transforming growth factor-alpha ("TGFα"), neuregulin-1, sonic hedgehog ("SHH"), Wnt3a, Wnt 5, ciliary neutrophic factor ("CNTF"), Notch ICD, or the like.

In some embodiments, the initial growth period can be followed by a second growth period of a set time interval, such as, for example, 1 day, 2 days, 3 days, 4 days, 6 days, 7 days, or more, or the like. During this second growth period, cells can be cultured with, for example, serum (FBS, HBS or synthetic serum substitutes) or a mix of bFGF, EGF and leukemia inhibitory factor ("LIF"), or any combination thereof, or the like. Likewise, in some embodiments the second growth period can be followed by a third growth period, or more. In certain embodiments, the type of cell culture media used during the third growth period can be the same as the type used during the initial growth period.

In one aspect of the present invention, a method for differentiation of a neural stem cell to a neuronal cell is provided, including providing a neural stem cell population and incubating the cell population under conditions suitable for differentiation of neural stem cells to neuronal cells. In one embodiment the differentiation conditions include initial priming for 7 days in the absence of attachment matrix and medium containing DMEM/F12 and B27 supplement and 1 uM all-trans-retinoic acid and/or 1 mM dBcAMP. After priming, the further differentiation conditions include the presence of a laminin attachment matrix and medium containing DMEM/F12 and B27 supplement. The progress of differentiation can be monitored by detecting one or more markers distinguishing neuronal cells from glial cells. In one embodiment the detectable marker is beta-III-tubulin. In another embodiment the detectable marker is MAP2. In still another embodiment the marker is GAD65. In still another embodiment the marker is pTH. In still another embodiment the marker is GFAP. In other embodiments, the marker includes one or more detectable markers. In other embodiments, the present invention includes a neuronally differentiated cell.

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
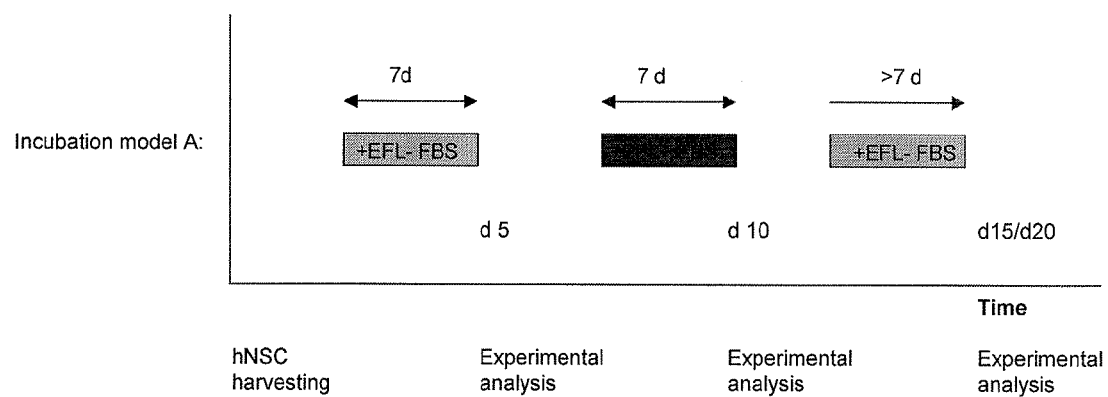
FIG. 1 shows the experimental protocol regarding media modification as performed in Example 1.

The present invention provides methods and systems for rapid amplification of human neural stem cells and subsequent differentiation into desired neuronal cell types. Examples of cell types obtained using methods of the present invention include neural stem cells (NSC), neuronal cells, pluripotent stem cells, multipotent stem cells, and cells having characteristics similar to those listed. The invention illustrates methods for rapid propagation by providing a human neural stem cell and incubating the cell under biphasic conditions that selectively support either proliferation or differentiation. Cell types are confirmed by examining the presence or absence of cell markers corresponding to the particular cell type or stage and optionally by viewing cell morphology or shape. Further, human neural stem cells that have been propagated in biphasic conditions are shown to selectively differentiate upon the addition of differentiation medium or conditions. The present invention is not limited to human neural cells obtained from human tissue but may be performed on cultured neural stem cells such as cell lines, any mammalian neural stem cells or any neural stem cells obtained from a vertebrate.

As will be appreciated by one skilled in the present art, the present invention provides pluripotent stem cells useful for a variety of medical applications and has a wide variety of therapeutic applications in medicine including human and veterinary medicine. Non-limiting examples of applications for the cells and methods of the present invention include cell based therapeutics of neurodegenerative disorders or neurotrauma, Alzheimer's disease and Parkinson's disease. Additional applications include treatment for patients suffering from stroke, brain injury or spinal cord injury. The methods of the present invention may be used to provide a replacement for defective or absent cells or may be used to develop a delivery method for therapeutic products.

In other aspects, the present invention is used for drug screening such as high throughput drug screening of potential prophylactic or therapeutic candidates. The methods and compositions of the present invention may be used to determine the effect of a compound on a neuronal cell by administering a compound to a neuronal cell generated using the methods of the present invention and detecting at least one phenotypic change. In still other embodiments, the methods of the present invention are used to monitor the progression of a precursor cell to a neuron. In other embodiments the methods of the present invention may be used to study the effect of a compound on a neural stem cell.

Terms used in the present invention may be found throughout texts and research articles within the fields of cell biology, developmental biology, stem cell biology, molecular biology, biochemistry and the like. Where there is a conflict in terminology, the specification and more preferably the following definitions shall control.

The term "cell population" as used herein refers to a group of cells having the same identifiable characteristics. The identifiable characteristics may include morphology, presence of a surface antigen, or relative abundance of particular mRNA and the like. A cell population may include a single cell, a group of cells grown from a single cell, or a common cell and the like.

The terms "detectable marker" or "cell marker" as used herein refers to characteristics that alone or in combination identify a cell or group of cells as belonging to a particular cell type or cell population. Markers may be detected by binding to a binding partner, such as an antibody having a label conjugated thereto, then observing directly or indirectly the label, by RT-PCR techniques with specific primers and the like.

The terms "develop", "differentiate" and "mature" as used herein all refer to the progression of a cell from the stage of having the potential to progress via the lineage to become a more specialized cell. The terms may be used interchangeably.

The terms "incubation under suitable conditions" as used herein refers to an incubation step where the cell is maintained in an environment to result in the desired effect. The environment may include compounds such as growth factors, substrates for cell attachment or cell growth, and the like.

The term "lineage" as used herein refers to all of the stages of development of a cell type, from the earliest precursor cell to a completely mature cell (i.e. specialized cell).

The term "medium capable of" as used herein refers to cell culture medium that includes the presence of compounds in an amount sufficient to provide the desired cell phenotype. The compounds and their amount can vary depending on cell type, desired cell phenotype, incubation time and can include growth factors and the like. Where particular concentrations are provided in the specification, the amounts are not intended to be specific limitations to the present invention but instead exemplary or preferred embodiments, because variations that produce the same effect are also intended to be encompassed by the present invention. Where particular concentrations are provided the present invention includes variations within 10%, 20%, 25% and 30% so long as the variations allow the desired result. Results may be tested using methods described herein.

The term "multipotent" as used herein refers to cell that can give rise to several other cell types, but those types are limited in number.

The term "neural stem cell" or "NSC" as used herein refers a cell derived from the nervous system which is characterized by having the ability of self-renewal and asymmetric division, which includes the ability to divide to produce two daughter cells with one being a self-renewed cell and the other having a development potential less than the renewed cell. The foregoing however is not to be construed to mean that each cell division of an NSC gives rise to asymmetrical division. It is possible that a division of an NSC can result only in self-renewal, or in the production of more developmentally restricted progeny only, or in the production of a self-renewed stem cell and a cell having restricted developmental potential. NSC's can be identified by detecting corresponding surface markers or by detecting relative abundance of mRNA compared to differentiated progeny. NSC's can be identified in comparison to neuronal cells using RT-PCR or immunoanalysis. More specifically, NSC's have a lower abundance of bIIItubulin, MAP2 and GFAP. NSC's can have a greater abundance of SOX1 mRNA.

The term "precursor cell" as used herein refers to any cell in a cell differentiation pathway that is capable of differentiating into a more mature or more specialized cell.

The term "pluripotent" as used herein refers to a cell that can develop into a variety of lineages. A pluripotent cell can create all cell types except for extra embryonic tissue, unlike a totipotent cell.

The present invention provides methods of obtaining neural stem cells, neuronal cells, or cells having characteristics of glial cells.

Embodiments of the invention provide techniques to propagate human neural stem cells ("hNSCs") as multipotent cells in significant numbers and then, for example, hNSCs differentiate the cells into particular types of nervous system cells. Certain embodiments include a method of fast propagation of hNSCs utilizing dynamic incubation of cells in a biphasic culture system where cells are initially grown for a set time interval, such as, for example, 1 day, 2 days, 3 days, 4 days, 6 days, 7 days, or more, or the like.

In certain embodiments, during the initial growth period the cells can be cultured with, for example, combinations of different bioactive molecules such as growth factors epidermal growth factor ("EGF"), transforming growth factor-alpha ("TGFα"), neuregulin-1, sonic hedgehog ("SHH"), Wnt3a, Wnt 5, ciliary neutrophic factor ("CNTF"), Notch ICD, or the like.

In some embodiments, the initial growth period can be followed by a second growth period of a set time interval, such as, for example, 1 day, 2 days, 3 days, 4 days, 6 days, 7 days, or more, or the like. During this second growth period, cells can be cultured with, for example, serum (FBS, HBS or synthetic serum supplements) or a mix of bFGF, EGF and leukemia inhibitory factor ("LIF"), or any combination thereof, or the like. Likewise, in some embodiments the second growth period can be followed by a third growth period, or more. In certain embodiments, the type of cell culture media used during the third growth period can be the same as the type used during the initial growth period.

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches found to function well in the practice of the invention, and thus can be considered to constitute examples of modes for its practice. However, those of skill in the art should, in light of the present disclosure, appreciate that many changes can be made in the specific embodiments that are disclosed and a like or similar result obtained without departing from the spirit and scope of the invention.

Example 1

Propagation of hNSC's hNSCs were alternately cultured in the presence (EFL+FBS) or absence (EFL−FBS) of fetal bovine serum (see FIG. 1). The media change was carried out on days 7 and 14 after plating. Growth of the cells included initial incubation in EFL−FBS, followed by incubation in EFL+FBS. Experimental analysis of hNSCs was carried out on days 5, 10, 15, and 20, if not otherwise indicated. The following abbreviations were used to designate specific growth factors: E=EGF; F=bFGF; L=LIF.

Medium 1 (−FBS): DMEM/F12 (1:1), 2% B27 (Gibco), 1% Pen-Strep (PAA). EGF (20 ng/ml, Peprotech), bFGF (20 ng/ml, Peprotech), LIF (10 ng/ml, Chemicon), heparin (5 ug/ml, Sigma).

Medium 2 (+FBS): DMEM/F12 (1:1), 2% B27 (Gibco), 1% Pen-Strep (PAA), 1% FBS (Gibco), EGF (20 ng/ml, Peprotech), bFGF (20 ng/ml, Peprotech), LIF (10 ng/ml, Chemicon), heparin (5 ug/ml, Sigma).

After 10 days, cells were counted using a hemocytometer and 150,000 cells from all samples were seeded in new wells.

Figure 2:
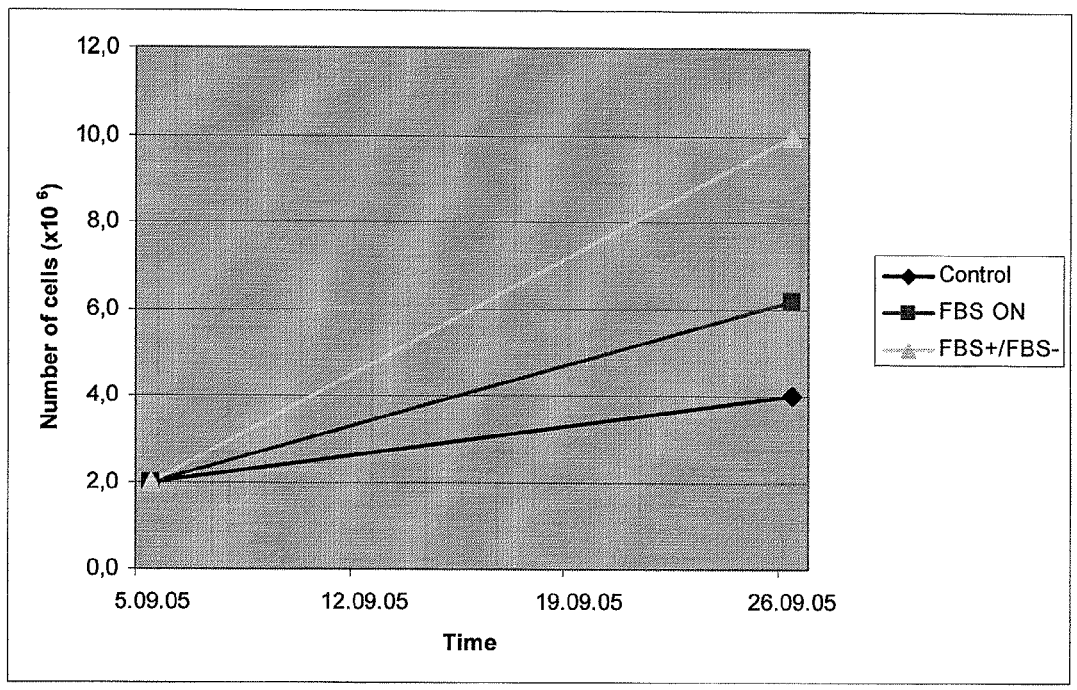
FIG. 2 depicts the growth rate of hNSCs grown as neurospheres according to the method of Example 1.

FIG. 2 shows the growth rate of hNSCs grown as neurospheres according to the method of Example 1. On days 5, 10, 15, and 20, if not otherwise indicated, neurospheres were dissociated using trypsin and single cells were counted using a hemocytometer. As controls, hNSCs were continuously grown either in the presence of serum and growth factors (FBS ON) or absence of serum, but in the presence of growth factors (control).

Example 2

Figure 3:
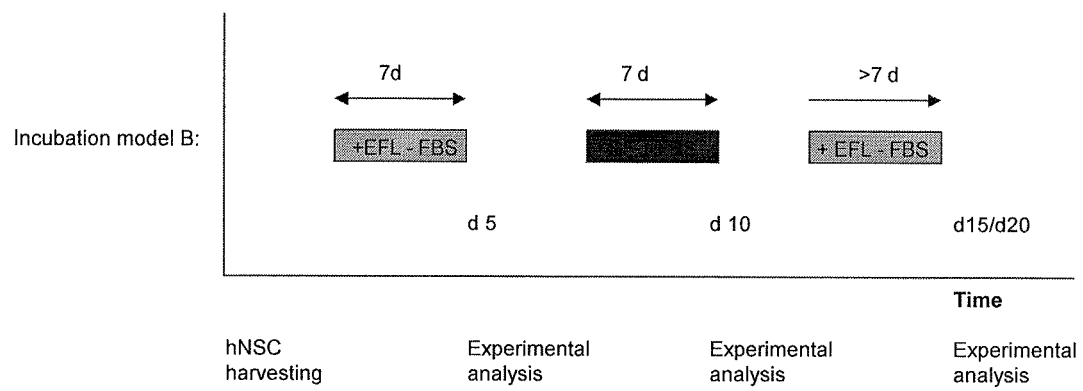
FIG. 3 shows the experimental protocol regarding media modification as performed in Example 2.

Propagation of hNSC's hNSC's were alternately cultured in media containing a certain growth factor and serum (GF+FBS) or in the media containing EFL but lacking the presence of fetal bovine serum (EFL−FBS) as shown in FIG. 3. The media was changed on days 7 and 14 after plating the cells. This example utilized an initial incubation in EFL−FBS, followed by incubation in media including FBS. Experimental analysis of hNSCs was carried out on days 5, 10, 15, and 20, if not otherwise indicated.

Human Neural stem cells were seeded at density of 100,000-150,000 cells/200 mm$^2$. Cells were grown alternately in 2 different conditions, each period lasting for 5 to 7 days. 10 to 14 days after plating, cells were counted and seeded to new plates at the same density (100,000-150,000 cells/200 mm$^2$).

Medium 1 (−GFs): DMEM/F12 (1:1), 2% B27 (Gibco), 1% Pen-Strep (PAA), EGF (20 ng/ml, Peprotech), bFGF (20 ng/ml, Peprotech), LIF (10 ng/ml, Chemicon), heparin (5 µg/ml, Sigma).

Medium 2 (+GFs): DMEM/F12 (1:1), 2% B27 (Gibco), 1% Pen-Strep (PAA), 1% FBS (Gibco)+one of the combination of growth factors (CNTF, Jagged, SHH, TGFa, Wnt1, Wnt5A, or all)

7 different combinations of growth factors were used: 2.1. CNTF (20 ng/ml, Peprotech); 2.2. Jagged (20 ng/ml, Peprotech); 2.3. SHH (20 ng/ml, Peprotech); 2.4. TGFa (20 ng/ml, Peprotech); 2.5 Wnt1 (20 ng/ml, R&D); 2.6 Wnt5A (20 ng/ml, R&D); and 2.7 all above.

After 14 days, cells were counted using hemocytometer and again 150,000 cells from all samples were seeded in new wells.

Figure 4:
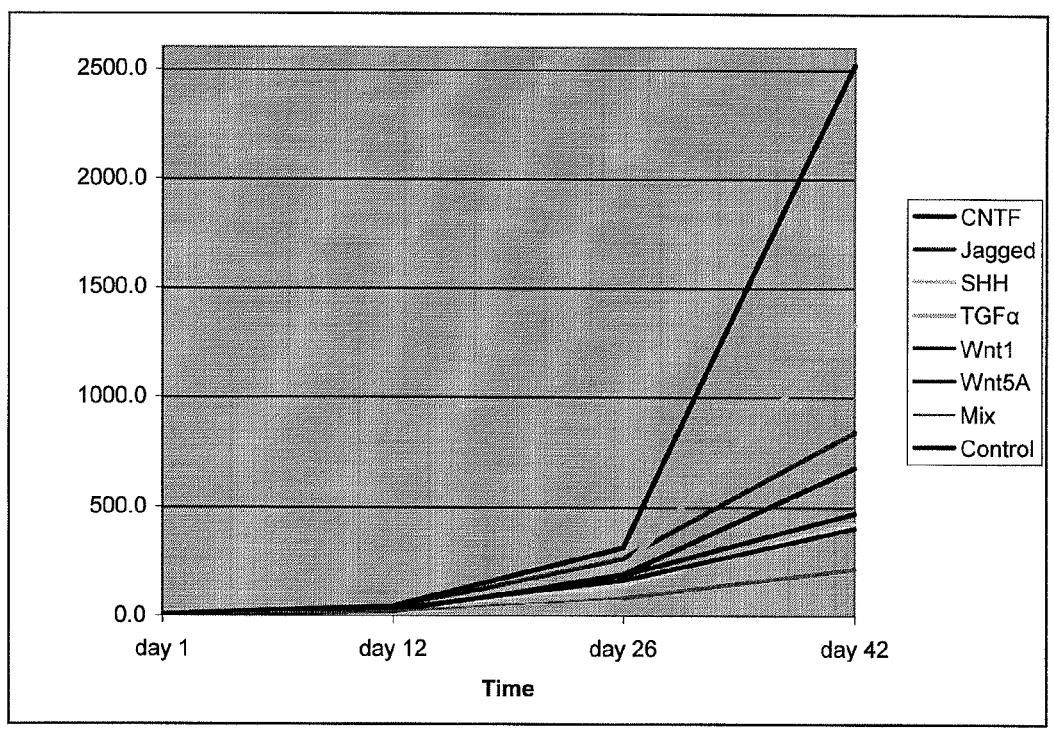
FIG. 4 shows the growth rate of hNSCs grown as neurospheres according to the method of Example 2.

FIG. 4 shows the growth rate of hNSCs grown as neurospheres according to the media schedule of FIG. 3. On days 5, 10, 15, and 20, if not otherwise indicated, neurospheres were dissociated using trypsin and single cells were counted using a hemocytometer. As a control, hNSCs were continuously grown in the absence of serum, but in the presence of growth factors EFL (control). The color code indicates the specific growth factor (GF) that was used in the GF+FBS mode. Abbreviations used: GF, growth factor; CNTF, ciliary neurotrophic factor; Jagged, SHH, sonic hedgehog; TGFα, transforming growth factor alpha; Wnt1, wingless-type MMTV integration site family, member 1; Wnt5A wingless-type MMTV integration site family, member 15a; or combined (CNTF, Jagged, SHH, TGFα, Wnt1, Wnt5A), E, EGF; F, bFGF; L, LIF.

Example 3

Figure 5:
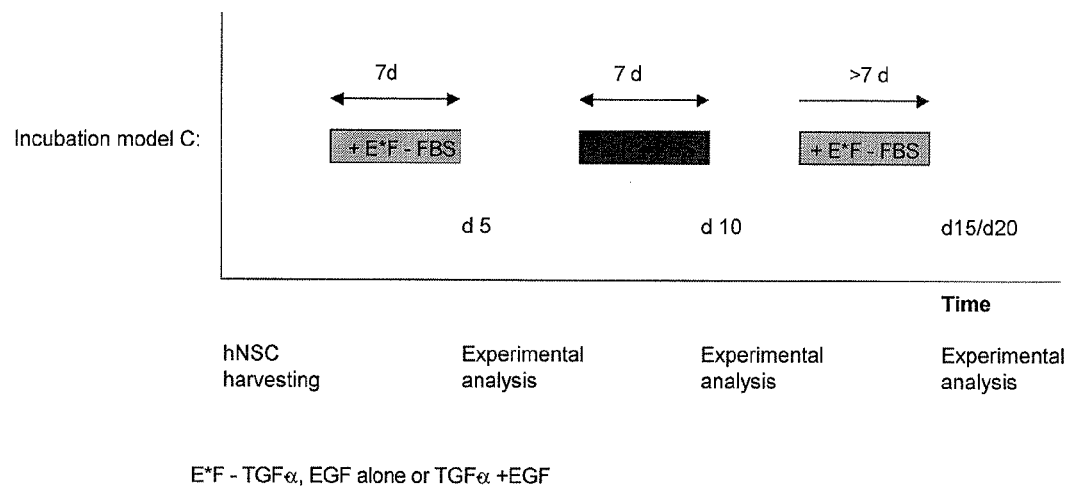
FIG. 5 shows the experimental protocol regarding media modification as performed in Example 3.

Propagation of hNSC's hNSC's were alternately cultured in media containing EGF or TGFα and bFGF and serum (E*F+FBS) or in media containing growth factors but lacking FBS (E*F−FBS) as shown in FIG. 5. Incubation mode C refers to initial incubation in E*F−FBS, followed by incubation in E*F+FBS. Experimental analysis of hNSCs was carried out on days 5, 10, 15, and 20, if not otherwise indicated. As a control, hNSC's were continuously grown in the absence of serum, but in the presence of growth factors EFL (control).

hNSC's were seeded at a density of 100,000-150,000 cells/200 mm$^2$. Cells were grown alternately in 2 different conditions, each period lasting for 5 to 7 days. 10 to 14 days after plating, cells were counted and seeded to new plates at the same density (100,000-150,000 cells/200 mm$^2$).

Medium 1 (−T, TE, E or C): DMEM/F12 (1:1), 2% B27 (Gibco), 1% Pen-Strep (PAA). EGF (20 ng/ml, Peprotech), bFGF (20 ng/ml, Peprotech), LIF (10 ng/ml, Chemicon), heparin (5 ug/ml, Sigma). Abbreviations used: T, TGFα; E, EGF; C, EGF+bFGF+LIF.

Medium 2 (+T, TE, E or C): DMEM/F12 (1:1), 2% B27 (Gibco), 1% Pen-Strep (PAA), 1% FBS (Gibco)+one of the combination of growth factors (T, TE, E or C). Abbreviations used: T, TGFα; E, EGF; C, EGF+bFGF+LIF.

The 4 different combinations of growth factors were: 3.1. TGFα (20 ng/ml, Peprotech) (T); 3.2. TGF α (20 ng/ml, Peprotech), EGF (20 ng/ml, Peprotech) (TE); 3.3. EGF (20 ng/ml, Peprotech) (E); 3.4. EGF (20 ng/ml, Peprotech), bFGF (20 ng/ml, Peprotech), LIF (10 ng/ml, Chemicon), and heparin (5 ug/ml, Sigma) (C). Abbreviations used: T, TGFα; E, EGF; C, EGF+bFGF+LIF.

After 14 days, cells were counted using a hemocytometer, and 150,000 cells from all samples were seeded in new wells.

Figure 6:
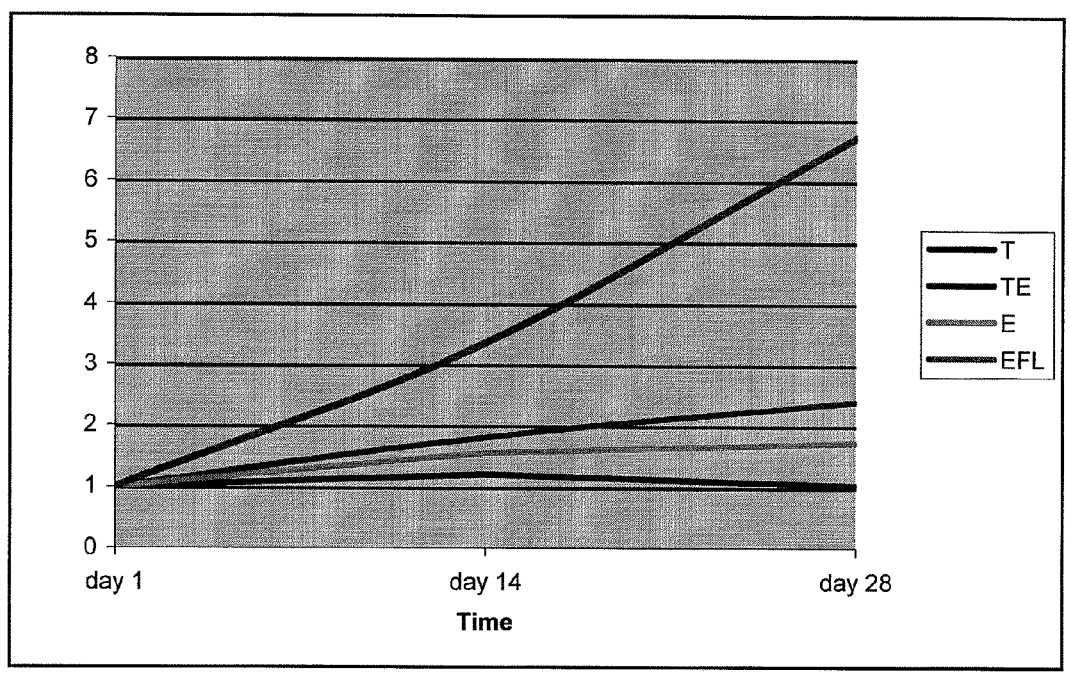
FIG. 6 depicts growth rate of hNSCs grown as neurospheres according to the method of Example 3.
Figure 7:
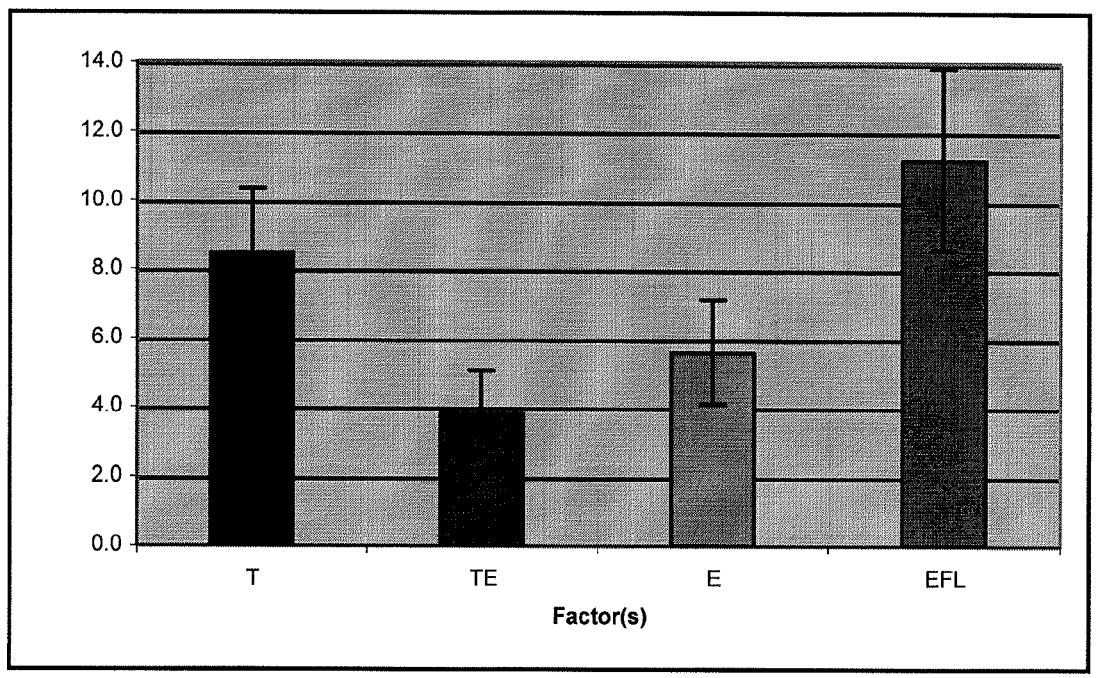
FIG. 7 shows the differentiation of hNSCs cultured according to the method of Example 3 using various growth factors.

FIG. 6 shows the growth rate of hNSCs grown as neurospheres according to the media schedule of FIG. 5. On days 5, 10, 15, and 20, if not otherwise indicated, neurospheres were dissociated using trypsin and single cells were counted using a hemocytometer. As a control, hNSC's were continuously grown in the absence of serum, but in the presence of growth factors EFL (control). The color code indicates the specific growth factor that was used in the E*F+FBS mode or control (EFL).

FIG. 6 shows the differentiation efficiency of hNSC's when cultured according to the method shown in FIG. 5. Differentiation was initiated by plating cells onto laminin coated tissue culture plates in the growth media containing no growth factors. Cells were fixed with 4% paraformaldehyde in PBS, 14 days after plating, then immunostained. An antibody against bIII-tubulin was used to detect neurons, and anti-GFAP was used to detect astrocytes. Abbreviations: E*, EGF, TGFα, alone or combined; F, bFGF. P<0.05 between different experiments.

Example 4

Differentiation of hNSC's hNSC's derived via the methods of Example 1 and 2 were plated onto laminin coated (incubated with laminin solution [(Roche, 0.02 mg/ml) 60 minutes at 37 C)] slides. After coating, the slides were washed with 1×PBS once. Growth media containing no growth factors (DMEM/F12 (Gibco), 2% B27(Gibco), Pen-Strep) was used. The media was changed every other day. After 14 days, cells were fixed with 4% paraformaldehyde in PBS and immunostained. Antibodies against bIII-tubulin and MAP-2 were used to detect neurons, anti-GFAP to detect astrocytes. Then one of the following: β-TubIII (Covance MRB-435P, rabbit, 1:2000); GFAP (Chemicon MAB360, mouse, 1:400); MAP2 (Chemicon AB5622, rabbit, 1:800). Cells were then counterstained with DAPI.

Figure 8:
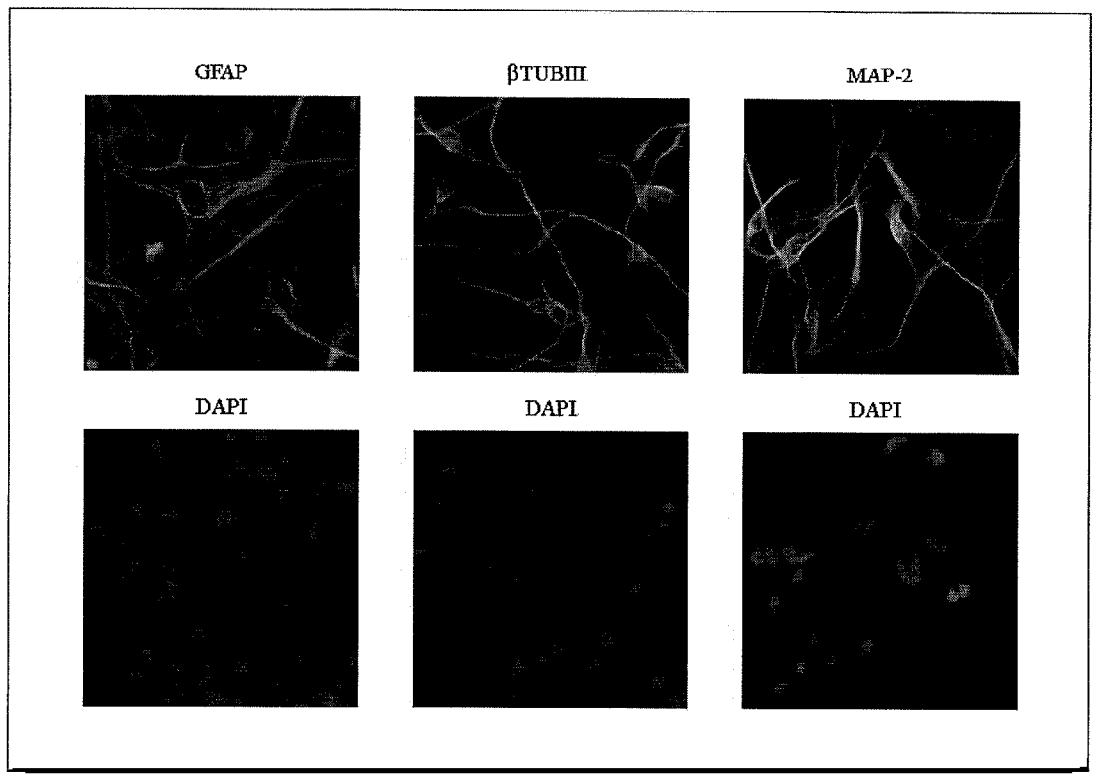
FIG. 8 depicts differentiation of hNSC's to neurons and astrocytes, cultured according to the methods of Examples 1 and 2.

The results are shown in FIG. 8. hNSCs differentiate to neurons and astrocytes being cultured according to conditions of the biphasic culture systems A and B. Antibodies against bIII-tubulin (green, top middle) and MAP-2 (green, top right) were used to detect neurons, anti-GFAP (green, top left) to detect astrocytes. Cells were counterstained with DAPI (blue).

Example 5

Differentiation of hNSC's hNSC's (derived via the methods of Example 1 and 2) from ½ of a 75 cm² flask were used for each differentiation condition. 35 mm Petri dishes were used to avoid cells attaching to plastic during differentiation. Growth media used was: DMEM/F12 (Gibco), 2% B27 (Gibco), and Pen-Strep; plus one of 6 different conditions as in the Table 1 below.

TABLE 1

Media Conditions

| No | Factor(s) | Concentration | Code |
|---|---|---|---|
| 1 | EGF + FGF (Peprotech) + LIF (Chemicon) | 20 ng/ml/20 ng/ml/ 10 ng/ml | EFL |
| 2 | RA + cAMP (Applichem) | 500 nM/1 mM | RC |
| 3 | RA + cAMP (Applichem) + BDNF (Peprotech) | 500 nM/1 mM/50 ng/ml | RCB |
| 4 | RA + cAMP (Applichem) + GDNF (Peprotech) | 500 nM/1 mM/50 ng/ml | RCG |
| 5 | RA + cAMP (Applichem) + NGF (Peprotech) | 500 nM/1 mM/50 ng/ml | RCN |
| 6 | RA + cAMP (Applichem) + NT-3 (Peprotech) | 500 nM/1 mM/50 ng/ml | RCT |

After 14 days, cells were fixed with 4% paraformaldehyde in PBS and immunostained. Antibodies against bIII-tubulin were used to detect neurons. The following were added: β-TubIII (Covance MRB-435P, rabbit, 1:2000); GFAP (Chemicon MAB360, mouse, 1:400); or MAP2 (Chemicon AB5622, rabbit, 1:800).

Figure 9:
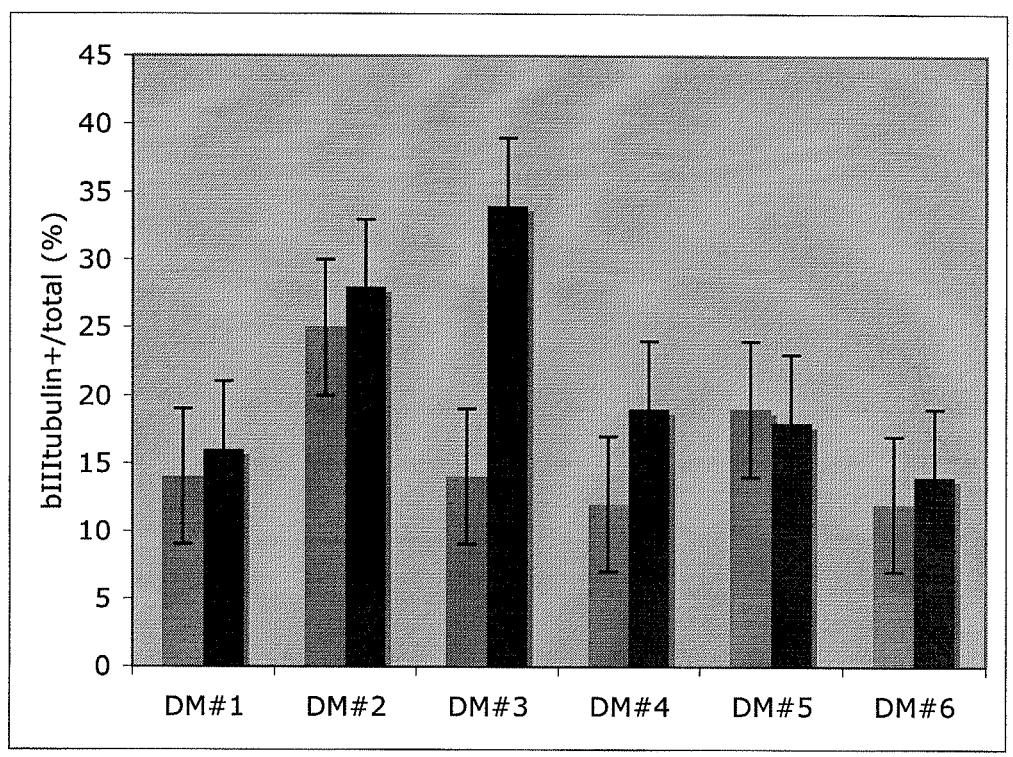
FIG. 9 shows a graph illustrating the changes (in percentage) in numbers of β-TubIII immunoreactive cells upon differentiation of hNSC's according to Example 4.

Cells were then counterstained with DAPI. The results are shown in FIG. 9. The figure illustrates changes (in percentage) in numbers of β-TubIII immunoreactive cells upon differentiation of hNSC's. Immunostaining revealed that "priming" of human neural stem cells in Petri dishes does not affect their potential to differentiate to neurons. Differentiation was initiated by harvesting cells in Petri dishes for 7 days after which cells were plated onto laminin coated tissue culture plates in the growth media containing no growth factors. As a control, differentiation was initiated by plating cells directly onto laminin coated tissue culture plates in the growth media containing no growth factors. Abbreviations used: RC=retinoic acid+dBcAMP; B=BDNF; G=GDNF; N=NGF, T=NT-3.

Example 6

Characterization of hNSC-Derived to TH+ and GABA+ Neurons hNSC's were propagated according to the method of Example 1 and differentiated according to the method of Example 5. hNSC-derived bIIItubublin+cells. hNSC-derived bIIItubulin+ cells were immunostained with TH and GAD65 antibodies. Condition where cells were differentiated 14 days on laminin-coated tissue culture dishes without the addition of any growth factors nor sera (DM#0) were used as control. The results are shown in Table 2 below.

TABLE 2

Quantitative analysis of TH+ and GAD65+ neurons upon differentiation using DM#3 and DM#4 media.

| Differentiation Media | TH+/ bIIItubulin + cells (%) | GAD65+/ bIIItubulin + cells (%) |
|---|---|---|
| DM#1 | 38 ± 6 | 75 ± 4 |
| DM#3 | 43 ± 8 | ND |
| DM#4 | <1 ± 1 | 84 ± 9 |

The Table 3 illustrates that DM#3 supported TH+ differentiation and DM#4 enhanced GABA+ (GAD65+) neuronal differentiation. These differentiated cells were also positive for tubulin βIII and MAP2. In addition, hNSC-derived TH+ cells did not co-express GABA or markers for astrocytes and oligodendrocytes such as, GFAP and O4, respectively. Similar findings were true to GABA+ cells. Using DM#0, 1, 2, 5 and 6 treatments, the numbers of GABA+ and TH+ neurons did not reach beyond <1% of total bIIItubulin+ cells.

Figure 10:
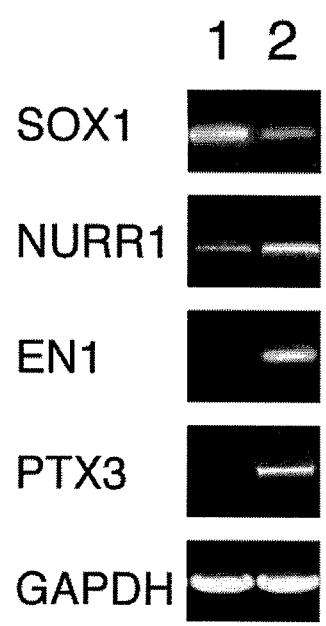
FIG. 10 shows expression of genes functioning in the biosynthesis of dopamine neurotransmitter systems. Upon differentiation according to the method of Example 5, cells were subjected to RT-PCR analysis of expression and semiquantitative levels of 3 genes governing the dopamine biosynthesis pathway, namely NURR1, EN1, and PTX3. The graph shows RT-PCR analysis data of 4 analyzed genes. Samples were normalized to the amount of GAPDH.

During differentiating hNSCs to TH+ neurons, the change of several markers was analyzed by semiquantitative RT-PCR (FIG. 10). The neural progenitor-marker Sox1 was strongly up-regulated already in proliferating hNSCs, whereas the expression of dopaminergic neuronal markers, such as NURR1, EN1, and PTX3 were prominent DM#3-differentiated neuronal cultures 7D post-treatment.

Figure 11:
FIG. 11 shows an expression analysis of genes functioning in the biosynthesis of GABAergic neurotransmitter systems. Upon differentiation according to the method of Example 5, cells were subjected to RT-PCR analysis of expression of 1 gene governing in the GABAergic biosynthesis pathway, namely PITX2. The graph shows RT-PCR analysis of 2 analyzed genes. Samples were normalized to the amount of GAPDH.
Figure 12:
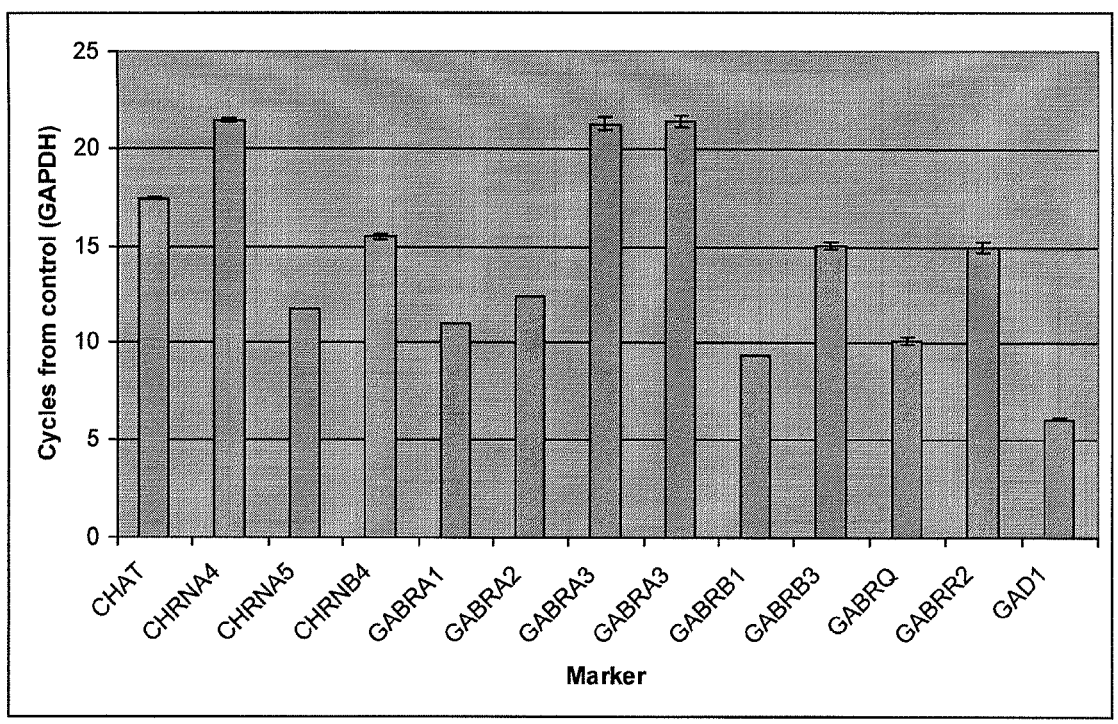
FIG. 12 shows an expression analysis of genes functioning in the biosynthesis of cholinergic and GABAergic neurotransmitter systems. Upon differentiation according to the method of Examples 5, cells were subjected to qPCR analysis of expression and quantitative levels of 4 genes functioning in the cholinergic biosynthesis pathway, and of 9 genes functioning in the GABAergic biosynthesis pathway. The graph shows qPCR cycle threshold values of 13 analyzed genes. Samples were normalized to the amount of GAPDH.
Figure 13:
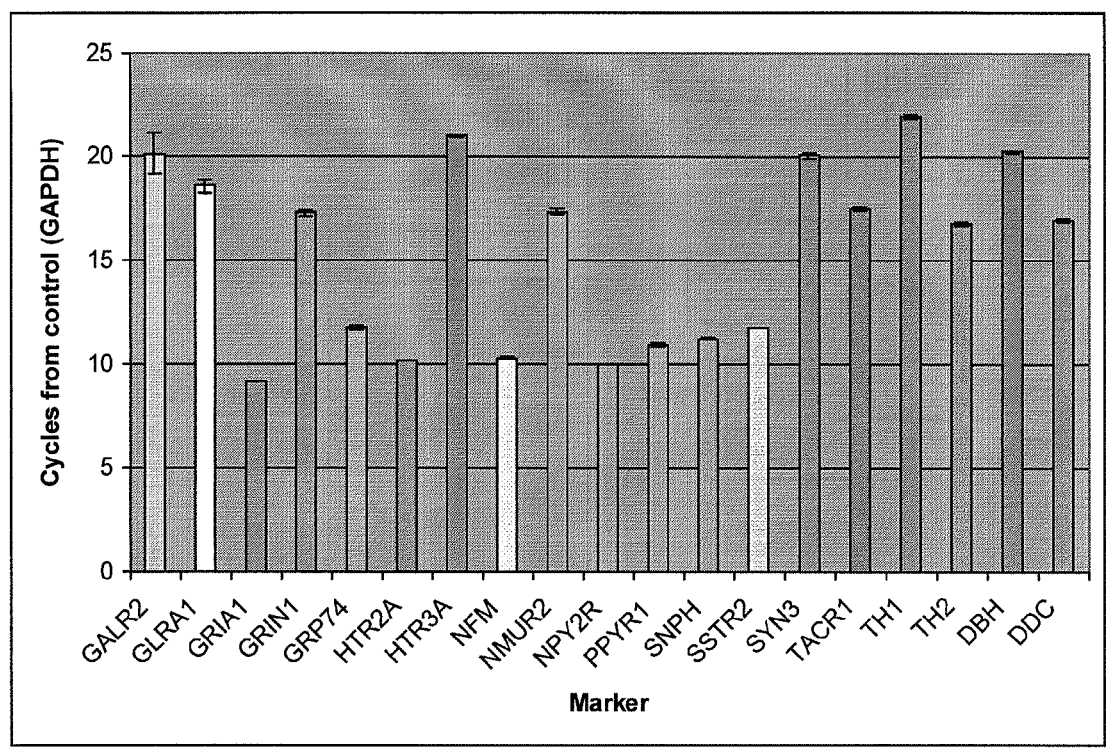
FIG. 13 shows an expression analysis of genes functioning in the biosynthesis of glycinergic, glutamatergic, serotonergic, and dopaminergic neurotransmitter systems. Upon differentiation according to the method of Examples 5, cells were subjected to qPCR analysis of expression and quantitative levels of 19 genes functioning in the biosynthesis pathway of different neurotransmitter systems. The graph shows qPCR cycle threshold values of 19 analyzed genes. Samples were normalized to the amount of GAPDH.

During differentiating hNSCs to GABA+ neurons, the change of several markers was analyzed by semiquantitative RT-PCR (FIG. 10). In DM#4 differentiated cultures, a significant increase in GABAergic neuron-specific transcription factor PITX2 mRNA was detected 7D after induction of differentiation (FIG. 11). Immunoanalysis GAD65 is one of the target genes of PITX2 activity.

The RT-PCR results support the IHC data indicating that the developed protocols are suitable for generation of dopaminergic (DA) and GABAergc neurons

Example 7

Phenotypic Analysis of Differentiated hNSC's Using RT-PCR Analysis hNSC's were propagated according to the method of Example 1. Without triturating, spheres from ½ of 75 cm² flask were used for each differentiation condition. 35 mm Petri dishes were used to avoid cells attaching to plastic during differentiation. The media used included DMEM/F12 (Gibco), 2% B27 (Gibco), Pen-Strep; +RA, and the differentiation period was 7 days.

Cells were then lysed (directly on plastic) and the RNA extracted using RNA Micro Kit (Ambion). cDNA was synthesized with First Strand Kit (Invitrogen).

The PCR protocol used was as follows: Platinum SYBR Green qPCR SuperMix-UDG (Invitrogen). PCR program: U-incubation at 50° C. for 2 min; polymerase activation at 95° C. for 2 min; cycling at 95° C. for 5 sec, 60 C for 10 sec and 72 C for 10 sec; 45 cycles (CHAT, DBH, TH: 50 cycles). Primers used are listed in Table 4. All primers are downloadable from Primer Bank database: http://pga.mgh.harvard.edu/primerbank/index.html

TABLE 3

Synthetic Primers

| SEQ | Receptor | Sense | Antisense |
|---|---|---|---|
| | | Acetylcholine Receptors | |
| 1 | CHRNA4 | GGCCTTCCTGCAAGTCACC | |
| 2 | CHRNA4 | | ATCGTCTCGGGGAACACAGT |
| 3 | CHRNA5 | ACGTTTTGAAGGGACCAGTACG | |
| 4 | CHRNA5 | | CACTCACAATCTCCCATTCTCC |
| 5 | CHRNB | TGACATCGTGCTTTACAACAACG | |
| 6 | CHRNB | | CGTGTGGTCATAGGTCCAGG |
| | | Benzodiazepine Receptors | |
| 7 | GABRA2 | AGTGGCTGTTGCCAATTATGC | |
| 8 | GABRA2 | | GGACTGACCCCTAATACAGGTT |
| 9 | GABRA3 | GTCACTGTTACATGACCAGCC | |
| 10 | GABRA3 | | CGTCCAGAAGACGATCCAAGAT |
| | | GABA-A Receptors | |
| 11 | GABRA1 | AGAAAAACAACACTTACGCTCCA | |
| 12 | GABRA1 | | GGGCTTGACCTCTTTAGGTTC |
| 13 | GABRB1 | GTACAAAATCGAGAGAGTCTGGG | |
| 14 | GABRB1 | | GCGAATGTCATATCCTTTGAGCA |
| 15 | GABRB3 | CTTGACAATCGAGTGGCTGA | |
| 16 | GABRB3 | | CAATCCTTTCCACTCCGGTA |
| 17 | GABRQ | ACATCGTGATCGTGTAGTCCA | |
| 18 | GABRQ | | TCCCGAAATTCCACTTCGAGT |
| 19 | GABRR2 | TGCCTGCCAGAGTTTCACTG | |
| 20 | GABRR2 | | CACACATGCACGGGAACTTC |
| | | Galanin Receptors | |
| 21 | GALR2 | GCCCTACCTGAGCTACTACC | |
| 22 | GALR2 | | GAGGATCATGCGTGTCACCTT |
| | | Glycine Receptors | |
| 23 | GLRA1 | CAGTGAACGTGAGCTGCAAC | |
| 24 | GLRA1 | | TCCAGAGAGTCGTCAGGGTAT |
| 25 | GLRA3 | TCGGGATTTTACTTCTGGGAAGC | |
| 26 | GLRA3 | | GATAGAGCCGAAACTGTTGATGA |
| | | Glutamate Receptors | |
| 27 | GRIA1 | GGTCTGCCCTGAGAAATCCAG | |
| 28 | GRIA1 | | CTCGCCCTTGTCGTACCAC |
| 29 | GRIN1 | AGGAACCCCTCGGACAAGTT | |
| 30 | GRIN1 | | CTCTCCAGTCGTCACCAGGT |

TABLE 3-continued

Synthetic Primers

| SEQ | Receptor | Sense | Antisense |
|---|---|---|---|

Neuropeptide Receptors

| 31 | GPR74 | TGGGTCCTAGCCATCACCATT | |
| 32 | GPR74 | | GCCCTGAAGAGTGAAATTCCA |

Neuropeptide Y Receptors

| 33 | NPY2R | ATGGGTCCAATAGGTGCAGAG | |
| 34 | NPY2R | | AGCAGTAGGCCAATATGAGAACA |
| 35 | PPYR1 | GGTCCTGGGTAACCTCTGC | |
| 36 | PPYR1 | | GAGACCGTCACCGACATGC |

Serotonin Receptors

| 37 | HTR2A | GCTCAACTACGAACTCCCTAATG | |
| 38 | HTR2A | | AGAGGCACCCTTCACAGGAA |
| 39 | HTR3A | GCTTGCCAGAAAAGGTGAAATC | |
| 40 | HTR3A | | GGCGGATGACCACATAGAACTT |

Somatostatin Receptors

| 41 | SSTR2 | GTCACCCGAATGGTGTCCATC | |
| 42 | SSTR2 | | ATTTGTCCTGCTTACTGTCACTC |

Tachykinin Receptors

| 43 | TACR1 | CACAACGAATGGTACTACGGC | |
| 44 | TACR1 | | CTCTGCTGGGCATGGTCTC |

Neurotransmitter Biosynthesis

| 45 | CHAT | CGTAAGATGGCAGCAAAAACTC | |
| 46 | CHAT | | GCCAGGCGGTTGTTGAGAT |
| 47 | GAD1 | GCCAAACAGAAGGGATATGTTCC | |
| 48 | GAD1 | | GCCCATCATCTTGTGAGGGTT |
| 49 | GAD2 | GGCTTTTGGTCTTTCGGGTC | |
| 50 | GAD2 | | TTCTCGGCGTCTCCGTAGAG |
| 51 | TH | GAGACGTTTGAAGCCAAAATCC | |
| 52 | TH | | AGGTCAGGGTCGAACTTGGT |
| 53 | DBH | ACTGGCTACTGCACGGACAAG | |
| 54 | DBH | | CTTTCTCCCAGTCAGGTGTGT |

Neurotransmitter Secretion

| 55 | SNPH | CAGCAGCCGATGACACACT | |
| 56 | SNPH | | GCACGAAGTCTGTCTGGATGG |
| 57 | SYN3 | CAGCAGCAAAGGTCACCAG | |
| 58 | SYN3 | | GGCTGTTAGTCAGGGACTGAG |

Example 8

Proliferation of Neural Stem Cells Treated with Various Bioactive Molecules Human neural stem cells are most routinely grown in medium supplemented with EGF and bFGF (and LIF). To analyze whether influencing signaling pathways with other growth factors can also support the proliferation of neural progenitor cells in undifferentiated state, growth conditions were alternated every 7 days. Cells were grown for 16 weeks and counted regularly every two weeks. During the first week (also third, fifth week, etc.) the cells were grown with different growth factors and 1% FBS in culture media. 8 different treatments were used: CNTF, Jagged-1, SHH, TGFa, Wnt1, Wnt5a, mix (CNTF, Jagged, SHH and Wnt-1) and combination of EGF, bFGF, LIF as control. During the second week (also fourth, sixth week, etc.) the cells were switched to routine growth medium (EGF, bFGF, LIF, no FBS). Cells were counted 8 times. During the first 8 weeks the cells proliferated at a quite similar rate, with only the control cells were growing slightly faster (data not shown). During the next 8 weeks, it was clearly seen that with control medium, cells were growing remarkably faster (FIG. 4). At the last time point analyzed, 5 times more cells were grown with control medium than under any other conditions. Surprisingly, the mix of four factors (CNTF, Jagged, SHH and Wnt1) supported the cell growth most weakly. All the factors used alone gave quite similar results; Wnt1, TGFa and Jagged-1 being slightly more efficient than the others. From these results was concluded that none of the tested conditions was supporting the proliferation of neural progenitor cells as efficiently as the combination of EGF, bFGF and LIF.

Example 7

Differentiation of Neural Stem Cells to Neurons and Astrocytes

Next, how the stimulation of signaling pathways affects the commitment of human neural stem cells to neuronal and glial lineages was examined. For differentiation, samples of cells grown in all 8 conditions were removed from proliferating cell populations (after 8 and 12 weeks in culture) and plated onto laminin coated coverslips. All additional factors were excluded from culture medium and cells were grown for 14 days. Next, cells were fixed and stained for neural and glial markers as described previously. Examples of immunocytochemistry analysis can be seen on FIG. 8. In differentiated cultures, cells were found to be positive for neuronal (bTubIII, MAP-2) and astrocyte markers (GFAP). No cells were detected as positive for oligodendrocyte marker O4. After immunostaining, cells from 3 random fields were counted and their differentiation potential was estimated according to the number of bTubIII positive cells present in samples. Results can be seen on FIG. 9. It is interesting to note, that while cells grown with different growth factors had significantly lower proliferation rates as compared to control, most of the cells had still retained differentiation potential similar to control cells. Cells grown with Wnt5a had the least percentage of bTubIII positive cells (33%), all the other conditions gave 41 to 47% of bTubIII positive cells (in control 45%). Taken together these data show that treatments for 16 weeks did not change the potential of neural progenitors to differentiate to bTubIII positive neuronal cells.

What is claimed is:

1. A method for propagating central nervous system multipotent progenitor and stem cells (NSCs) and their differentiation into neuronal cells, the method comprising:
   a) initiating a growth period by culturing NSCs in a serum-free medium comprising epidermal growth factor (EGF),
   b) culturing the NSCs from step a) in a proliferation medium comprising serum and epidermal growth factor (EGF), fibroblast growth factor (bFGF) and leukemia inhibitory factor (LIF); wherein the cultured conditions from steps a) and b) are alternated every 5 to 7 days, and
   c) differentiating the cells of b) by culturing the cells on medium containing no growth factors on a laminin coated matrix for cell attachment, wherein NSCs differentiate into neuronal cells.

2. A method for propagating central nervous system multipotent progenitor and stem cells (NSCs) and their differentiation into neuronal cells, the method comprising:
   a) culturing NSCs in a serum-free medium and in the presence of a proliferation supporting component comprising at least one growth factor selected from the group consisting of epidermal growth factor (EGF), transforming growth factor-alpha (TGF-α), neuregulin-1, sonic hedgehog (SHH), wingless-type MMTV integration site family member 3a (Wnt3a), wingless-type MMTV integration site family member 5 (Wnt 5), ciliary neutrophil factor (CNTF) and Notch integrity cellular domain (ICD),
   b) culturing the NSCs from step a) in medium comprising serum and a same or different proliferating supporting component; wherein the cultured conditions from steps a) and b) are alternated every 5 to 7 days, and
   c) differentiating the cells of step b) by culturing the cells on medium containing no growth factors on a laminin coated matrix for cell attachment, wherein NSCs differentiate into neuronal cells.

3. The method of claim 1, further comprising before step c):
   i) harvesting proliferating NSCs according to step b), and
   ii) priming the cells of i) by culturing the NSCs in the absence of a matrix for cell attachment in a differentiation medium comprising at least one neuronal differentiation supporting component selected from the group consisting of retinoic acid (RA), dibutyl cyclic adenosine monophosphate (dBcAMP), brain derived neutrophil factor (BDNF), glial cell derived neutrophil factor (GDNF), nerve growth factor (NGF) and neutrophin-3 (NT-3), wherein said priming initiates differentiation of the NSCs; and
   iii) transferring the primed NSCs to the medium containing no growth factors on a laminin coated matrix of claim 1, step c).

4. The method of claim 2, wherein the growth factor comprises epidermal growth factor (EGF), basic fibroblast growth factor (bFGF) and leukemia inhibitory factor (LIF).

5. The method of claim 2, wherein the serum free medium of step a) comprises EGF and the medium with serum of step b) comprises a mix of EGF, bFGF and LIF.

6. The method of claim 2, further comprising before step c):
   i) harvesting proliferating NSCs according to step b), and
   ii) culturing the NSCs on a substrate lacking a matrix for cell attachment and in a medium lacking the proliferation supporting component, wherein the medium comprises a neuronal differentiation supporting component selected from the group consisting of RA, dBcAMP, BDNF, GDNF, NGF, and NT-3 wherein the culturing of step ii) initiates differentiation of the NSCs.

7. The method of claim 3, wherein the neuronal differentiation support component comprises RA and dBcAMP and optionally BDNF.

8. The method of claim 6, wherein the additional step is conducted for about 7 days.

9. The method of claim 1, wherein after step b) and before step c), the NSCs are further cultured the serum-free medium of step a).

10. The method of claim 2, further comprising:
    i) harvesting proliferating NSCs after repeating steps a) and b),
    ii) priming the cells of i) by culturing
    the cells in the absence of a matrix for cell attachment in a differentiation medium comprising at least one neuronal differentiation supporting component selected from the group consisting of retinoic acid (RA), dibutyl cyclic adenosine monophosphate (dBcAMP), brain derived neutrophil factor (BDNF), glial cell derived neutrophil factor (GDNF), nerve growth factor (NGF) and neutrophin-3 (NT-3) and containing no growth factors, wherein said priming initiates differentiation of the NSCs; and
    iii) transferring the primed NSCs to the medium containing no growth factors on a laminin coated matrix of claim 2, step c).

* * * * *